United States Patent
Biddulph et al.

(10) Patent No.: US 11,602,462 B2
(45) Date of Patent: Mar. 14, 2023

(54) REVERSIBLE COMPRESSION GARMENT

(71) Applicant: Julius Zorn, Inc., Cuyahoga Falls, OH (US)

(72) Inventors: Greg Biddulph, Cuyahoga Falls, OH (US); Carla J. Blackman, Cuyahoga Falls, OH (US); Douglas R. Halley, Cuyahoga Falls, OH (US); Adrian Slattery, Cuyahoga Falls, OH (US)

(73) Assignee: Julius Zorn, Inc., Cuyahoga Falls, OH (US)

( * ) Notice: Subject to any disclaimer, the term of this patent is extended or adjusted under 35 U.S.C. 154(b) by 613 days.

(21) Appl. No.: 16/500,520

(22) PCT Filed: Apr. 5, 2018

(86) PCT No.: PCT/US2018/026205
§ 371 (c)(1),
(2) Date: Oct. 3, 2019

(87) PCT Pub. No.: WO2018/187538
PCT Pub. Date: Oct. 11, 2018

(65) Prior Publication Data
US 2020/0107968 A1     Apr. 9, 2020

Related U.S. Application Data

(60) Provisional application No. 62/482,435, filed on Apr. 6, 2017.

(51) Int. Cl.
*A61F 13/08* (2006.01)
*A61F 13/00* (2006.01)
*A61H 1/00* (2006.01)

(52) U.S. Cl.
CPC ...... *A61F 13/085* (2013.01); *A61F 13/00059* (2013.01); *A61H 1/008* (2013.01); *A61H 2201/165* (2013.01)

(58) Field of Classification Search
CPC ............. A61F 5/05841; A61F 5/0585; A61F 5/05866; A61F 5/05875; A61F 5/0109;
(Continued)

(56) References Cited

U.S. PATENT DOCUMENTS 2,574,678 A * 11/1951 Wilbur ............... A61F 5/03 2/60
2005/0192524 A1* 9/2005 Lipshaw ............ A61F 13/06 602/62

(Continued)

FOREIGN PATENT DOCUMENTS

| WO | WO 2011/066237 A1 | 6/2011 |
| WO | WO 2014/132127 A1 | 9/2014 |
| WO | WO 2016/205179 A2 | 12/2016 |

OTHER PUBLICATIONS

International Search Report of PCT/US2018/026205 dated Jun. 20, 2018.

*Primary Examiner* — Keri J Nelson
*Assistant Examiner* — Kevin S Albers
(74) *Attorney, Agent, or Firm* — Renner, Otto, Boisselle & Sklar, LLP

(57) ABSTRACT

A compression garment includes a main body including a central portion and a plurality of straps that extend from the central portion. The central portion has a lateral edge having first regions from which the straps extend from the central portion, and second regions from which the straps do not extend. A connecting portion is fixed to the main body and is fixed to at least a portion of the second regions. The straps are moveable to reverse the compression garment between a first state and a second state. The straps may be moveable around the connecting portion, or may be feedable through the connecting portion, to reverse the compression garment between the first state and the second state. The connecting portion and the main body may define a plurality of slits (Continued)

through which the straps are insertable to reverse the compression garment.

20 Claims, 9 Drawing Sheets

(58) Field of Classification Search
CPC .... A61F 5/0118; A61F 5/05816; A61F 5/058; A61F 5/05858; A61F 5/01; A61F 5/0106; A61F 5/0193; A61F 5/03; A61F 13/08; A61F 13/104; A61F 13/107; A61F 13/06; A61F 13/10; A61F 13/064; A61F 13/00059; A61F 13/102; A61F 13/108; A61F 13/085; A61H 2201/165
See application file for complete search history.

(56) References Cited

U.S. PATENT DOCUMENTS

| | | | | |
|---|---|---|---|---|
| 2014/0358055 A1* | 12/2014 | Mueller | ................ | A61F 5/0118 602/20 |
| 2015/0025424 A1* | 1/2015 | Richardson | ........... | A61F 13/085 601/84 |
| 2015/0148723 A1* | 5/2015 | Huff | .......................... | A61F 5/01 602/5 |
| 2016/0000612 A1* | 1/2016 | Cox | ...................... | A61F 13/085 602/62 |
| 2016/0058623 A1* | 3/2016 | Lipshaw | ............... | A61F 13/085 602/75 |
| 2017/0143526 A1* | 5/2017 | Gaylord | ................ | A61F 5/0118 |
| 2018/0092782 A1* | 4/2018 | Miller | ................... | A61F 13/108 |

* cited by examiner

REVERSIBLE COMPRESSION GARMENT

RELATED APPLICATION DATA

This application is a national stage application pursuant to 35 U.S.C. § 371 of PCT/US2018/026205 filed on Apr. 5, 2018, which claims the benefit of U.S. Provisional Application No. 62/482,435 filed Apr. 6, 2017, the contents of which are incorporated herein by reference.

FIELD OF INVENTION

The present invention relates to therapeutic compression garments worn to prevent fluid build-up in the limbs, and particularly relates to a reversible compression garment having straps that wrap around a patient's limb.

BACKGROUND OF THE INVENTION

Therapeutic compression garments are worn to prevent the build-up of fluid in the limbs, a condition commonly referred to as edema, and various types of vascular insufficiencies. Persons who may use such a garment include post-surgical patients, obese persons, and persons with ailments that impede circulation, such as Chronic Venous Insufficiency, Lymphedema and diabetics. Compression garments improve circulation and prevent fluid from collecting in the lower limb portions, such as in the feet and ankles (leg compression garment) or hands (arm compression garment). By improving circulation and reducing the propensity toward fluid build-up, compression garments relieve swelling and associated pain, prevent and help in the treatment of ulcers, and prevent other issues that can result from poor circulation in the limbs.

Various types of compression garments are known in the art. One type of compression garment is a tubular shaped, high elastic, knitted compression garment, which provides graduated compression when worn on a limb. High elastic compression garments offer only a minimal increase in working pressure allowing them to be easier to don. Depending upon the level of a patient's clinical involvement, such garments may, at times, not provide an adequate level of pressure to improve circulation or prevent edema in the limb.

Accordingly, more "low-elastic", stretch-limited compression garments also have been used to provide compression, but such garments likewise must be able to accommodate changes in compression based on changes in the size of the limb. Low-elastic garments have an advantage over elastic garments in that low-elastic garments provide an increased or higher working pressure in response to increased patient activity or limb edema. As a limb expands due to muscle expansion or edema, the expanded limb pushes up against the low-elastic garment, which is stretch-limited and therefore offers greater resistance as compared to high-elastic garments. This results in higher working pressure. The relatively high working pressure of low-elastic garments results in an improved vascular flow and edema containment. As a consequence of the high working pressure and limited stretch, low-elastic garments formed in a tubular shape can be considerably more difficult to don as compared to high-elastic garments.

To provide for a more dynamic compression that adjusts with changing situations and are easier to don, wrap-style low-elastic compression garments have been employed. Such garments may be wrapped around a limb and secured using a fastening device, such as a hook and loop mechanical fastening device. As such, they may be removed and re-wrapped with differing tensions to accommodate any changing compression needs. Wrapped compression garments may be configured with staggered compression straps or bands that are linked together by a central spine or region, the straps wrapping around the limb. The use of bands or straps provides substantial versatility in achieving a desired amount of compression, both as therapeutically required and to provide a more comfortable fit.

Conventional low-elastic wrapped compression garments with bands or straps, however, still have deficiencies related to providing a desired fit. It is desirable that there not be significant gaps between the straps in use. Any significant gaps constitute areas where compression is not applied, and thus provide areas where fluid may accumulate. In addition, users of compressions garments also desire the garments to match well with clothing. This, however, conventionally has required users to buy multiple compression garments of different colors or patterns. Accordingly, a reversible compression garment is desirable, which can afford two alternative looks. A readily reversible compression garment is shown in Applicant's PCT application Ser. No. PCT/US16/37339, filed on Jun. 14, 2016 and incorporated here by reference.

SUMMARY OF INVENTION

The present invention provides a low-elastic wrapped compression garment that is easy to don and provides suitable compression across a wide range of users and compression needs. The compression garment also is reversible to provide two alternative looks of the compression garment.

In exemplary embodiments, a low-elastic wrapped compression garment includes a main body including a central portion and a plurality of straps that extend from the central portion; the central portion including a lateral edge, the lateral edge having first regions from which the straps extend from the central portion, and second regions from which the straps do not extend; and a connecting portion that is fixed to the main body, the connecting portion being fixed to at least a portion of the second regions. The straps are moveable relative to the connecting portion to reverse the compression garment between a first state and a second state. The straps may be moveable around the connecting portion, or may be feedable through the connecting portion, to reverse the compression garment between the first state and the second state. The connecting portion and the main body may define a plurality of slits through which the straps are insertable to reverse the compression garment between the first state and the second state.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

DETAILED DESCRIPTION

Figure 1:
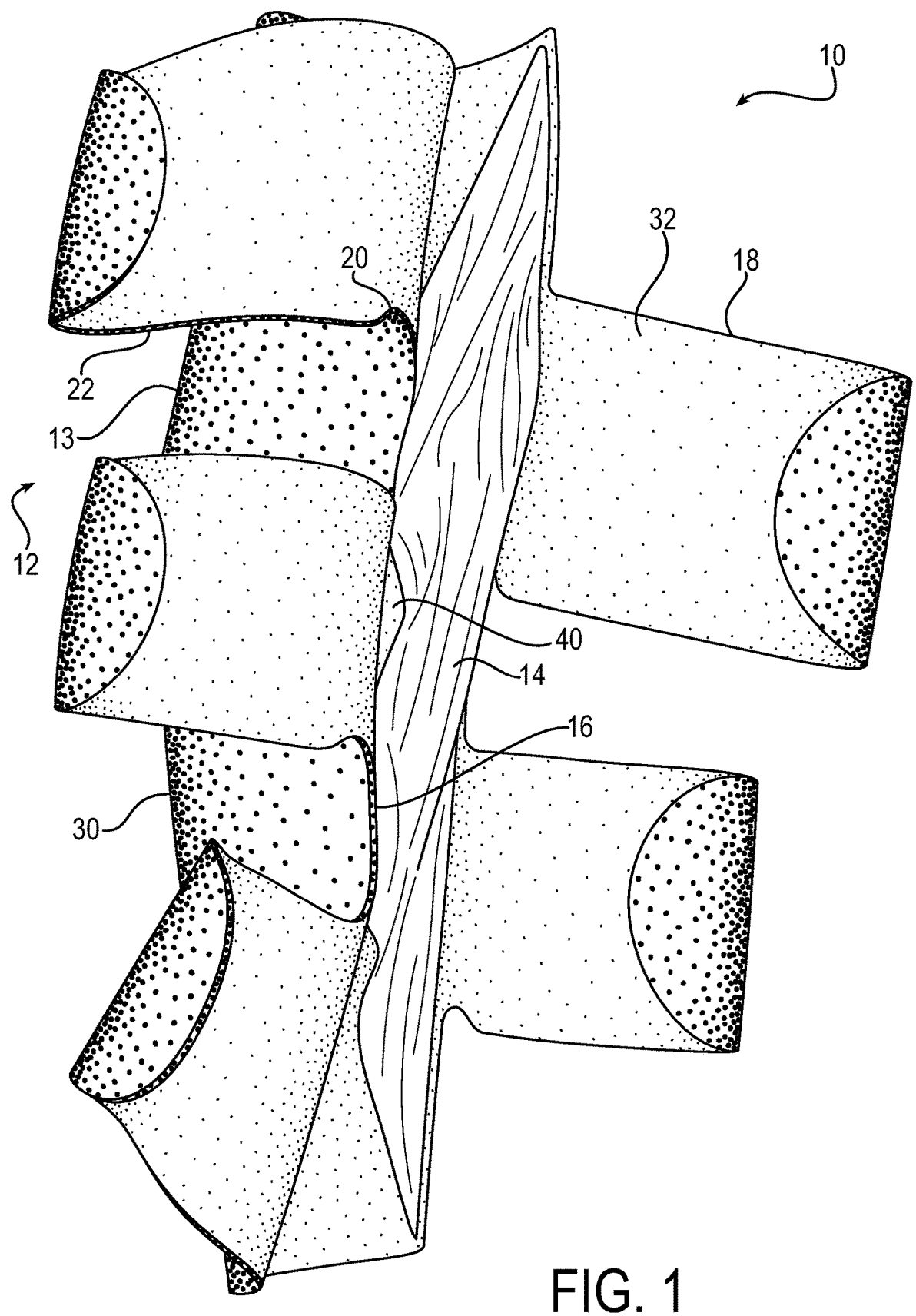
FIG. 1 is a drawing depicting an exemplary compression garment in accordance with embodiments of the present invention, with the compression garment being in a first state.

Embodiments of the present invention will now be described with reference to the drawings, wherein like reference numerals are used to refer to like elements throughout. It will be understood that the drawings are not necessarily to scale.

The present invention provides a low-elastic wrapped compression garment that is easy to don and provides suitable compression across a wide range of users and compression needs. The compression garment also is reversible to provide two alternative looks of the compression garment. In exemplary embodiments, a low-elastic wrapped compression garment includes a main body including a central portion and a plurality of straps that extend from the central portion; the central portion including a lateral edge, the lateral edge having first regions from which the straps extend from the central portion, and second regions from which the straps do not extend; and a connecting portion that is fixed to the main body, the connecting portion being fixed to at least a portion of the second regions. The straps are moveable relative to the connecting portion to reverse the compression garment between a first state and a second state. The straps may be moveable around the connecting portion, or may be feedable through the connecting portion, to reverse the compression garment between the first state and the second state. The connecting portion and the main body may define a plurality of slits through which the straps are insertable to reverse the compression garment between the first state and the second state.

Figure 2:
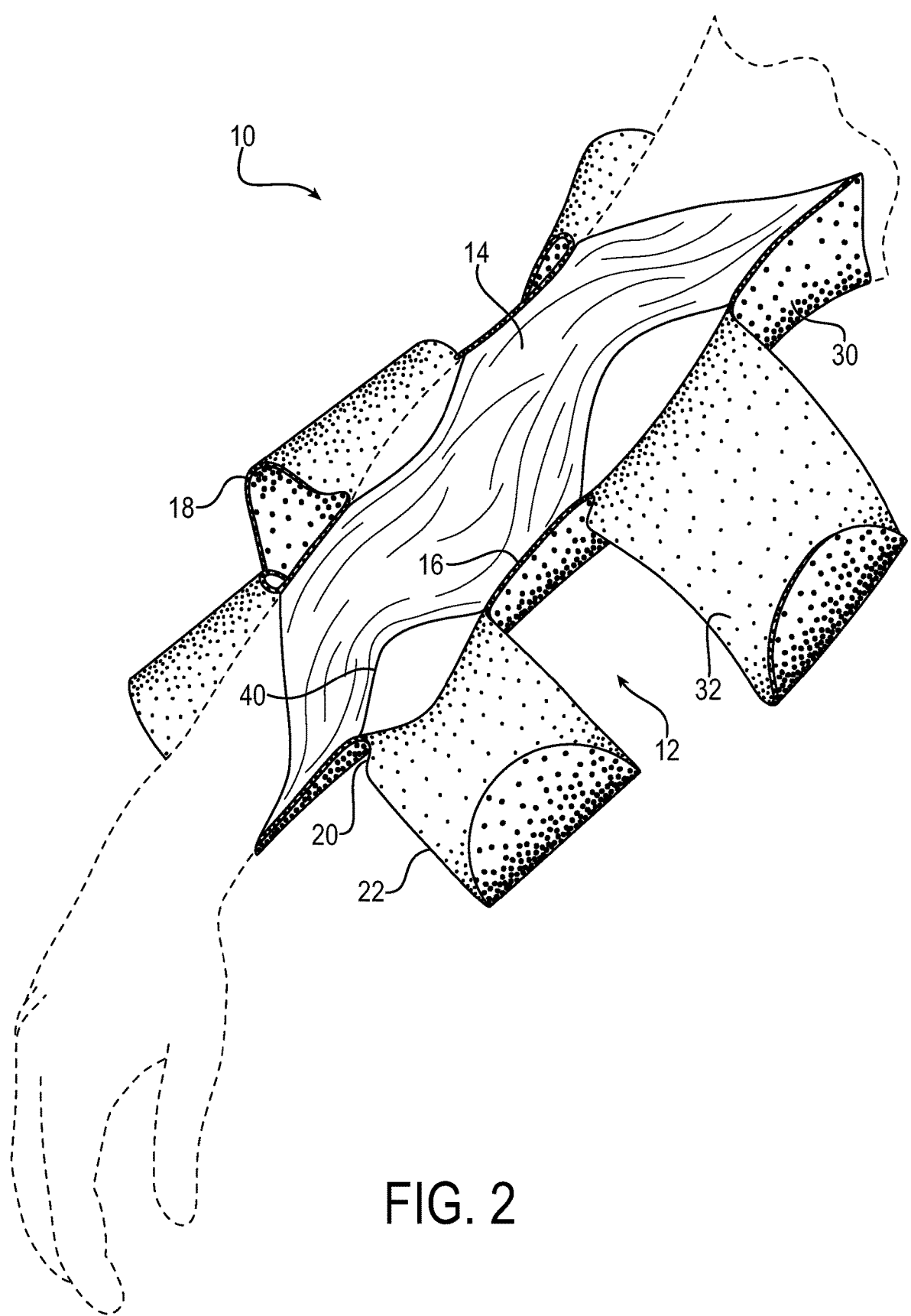
FIG. 2 is a drawing depicting the compression garment of FIG. 1 in a partially worn state, in which the compression garment is placed around a limb but the straps are not as yet secured.

Referring to the figures, FIG. 1 is a drawing depicting a compression garment 10 in accordance with embodiments of the present invention, and FIG. 2 is a drawing depicting the compression garment 10 in a partially worn state, in which the compression garment is placed around a limb but the straps are not as yet secured. In this example, an arm compression garment is shown, but the principles of this invention are not limited to any particular limb. The features of the invention may be utilized in connection with a compression garment extending over any desired length of any limb, such as for example a lower leg compression garment about the lower leg or calf, a leg compression that extends from the calf over the knee to around the thigh, and/or going down to or around the foot and/or ankle, around the upper and/or lower arm extending any desired length over the arm and/or wrist or hand, and the like. The precise size of the compression garment relative to the scope of the extension over the given limb will depend upon the compression needs.

The compression garment 10 may include a main body 12 and a connecting portion 14. The main body 12 may include central portion 13 having a lateral edge 16, and a plurality of straps 18 that extend from first regions of the lateral edge 16 of the central portion 13. The lateral edge further may include second regions between the straps, where no strap extends from the central portion. It will be appreciated that the precise number of straps may vary depending upon the size of the compression garment relative to the scope of an amount of a limb portion that is desired to be wrapped for compression.

Once wrapped around a limb, the straps may be secured to an opposite portion of the main body by a mechanical fastening system. Any suitable fastening means may be employed, and mechanical fastening tabs are particularly suitable. For example, the fastening system may be formed as hook-and-loop and similar type mechanical fastening elements. The straps may be pulled and secured to tension the straps in the wrapped position, resulting in a compression force being applied to the limb as described above. The straps are staggered such that when the straps are wrapped around the remainder of the limb, there is an overlap of the edges of adjacent straps in the wrapping around direction.

Where at least some of the straps 18 extend from the central portion 13 of the main body, a notch 20 may be provided so that adjacent straps may overlap without bunching of the strap material. In the example embodiment of the figures, at least one notch 20 may be provided adjacent to where a longitudinal edge 22 of one of the straps meets the lateral edge 16 of the central portion. Accordingly, when the compression garment is in a wrapped position, edges of adjacent straps that are associated with the at least one notch overlap. The overlapping of the straps is shown in figures described below (see particularly FIGS. 7 and 8). With such configuration, the straps are wrapped around a limb portion both without gaps between the straps, and without bunching of the strap material, resulting in an enhanced fit and comfort as compared to conventional configurations while maintaining full compression along the entirety of the compression garment.

The notches thus permit overlap of adjacent straps, but the amount of overlap is minimal as compared to conventional configurations, while still providing an effective gapless configuration. The amount of overlap may be ¼ inch or less, and may be as little as ⅛ inch. In this regard, the amount or degree of overlap is achieved regardless of the size of the compression garment. For example, a common amount of overlap may be present in a garment for a large limbed user and a small limbed user, and for a large limb (e.g., thigh garment) as compared to a small limb (e.g., calf or arm garment). Accordingly, the compression garment is substantially less bulky as compared to conventional configurations. In addition, with the notches 20 being located where the straps extend form the lateral edge 22 of the central portion of the main body, there is little tendency for the straps to move laterally relatively to each other. The present invention, therefore, provides a gapless configuration that has enhanced comfort and requires less material to manufacture.

As referenced above, the compression garment 10 further includes a connecting portion 14. The connecting portion 14 is fixed to the main body 12 by fixing the connection portion 14 to portions of the lateral edge 16 of the main body in regions between the straps, i.e., the referenced second regions of the lateral edge where the straps do not extend from the central portion of the main body. In one exemplary embodiment as illustrated in the figures, the connecting portion 14 may be configured in a "zig-zag" configuration that, with the main body, defines a space through which the limb is inserted. As such, the garment is non-flat and is not fully tubular, but the space defined between the main body and the connecting portion provides guiding surfaces for donning the compression garment. This is seen, for example, in FIG. 2 in which the compression garment is donned but the straps are not yet secured. In this state, the limb is between the central portion 13 of the main body 12 and the connecting portion 14. The connecting portion may be fixed to the main body by any suitable means, such as for example by sewing or gluing.

In the example shown, the connecting portion is connected to the second regions of the lateral edge (the regions from which straps do not extend) of the main body over the entirety of such regions where the straps are absent. This, however, need not be the case, and the connecting portion can be attached to the lateral edge spanning only part of such regions. In other words, only one or more sub-parts of the second regions of the lateral edge where the straps are absent need to be connected to the connecting portion. In addition, the connecting portion is illustrated as one piece in this example, but the connecting portion may be split into multiple pieces with each spanning a portion of second regions of the lateral edge.

In exemplary embodiments, the main body and the connecting portion are made of different materials having different properties. As is known in the art, compression materials may be considered as "short-stretch" or "long-stretch" as such terms of art are used for compression materials, and thus are commonly understood by those of ordinary skill in the art. In general, in exemplary embodiments the connecting portion 14 tends to be thinner and more elastic as compared to the main body, with the connecting portion 14 being a long-stretch material and the main body 12 being a short-stretch material. The connecting portion may be made of a single layer of elastic woven fabric. The main body may have a layered configuration that forms a limited stretch material. For example, the main body may employ layers of material that are bonded together, including an internal compressible layer sandwiched between a first woven fabric layer 30 and a second woven fabric layer 32 on opposite faces of the internal compressible layer. The internal compressible layer may be made of a synthetic rubber type material or the like, with neoprene being a suitable example. The connecting portion and woven fabric layers of the main body may be made of nylon loop type fabric materials or the like, with spandex materials being a suitable example.

The thinness and higher elasticity of the connecting portion aids in donning the garment, while the more limited stretch nature of the main body provides the compression when the straps are secured. A significant advantage of including the connecting portion is that it aids substantially in donning the compression garment, which otherwise can be difficult for users of compression garments. A challenge in donning compression garments is in properly aligning the garment relative to the limb portion for the most effective compression. The presence of the highly elastic connecting portion leads the garment to an initial position about the limb that is most suitable for compression once the main body is fully wrapped and the straps are secured.

The level of working pressure provided by the limited stretch nature of the compression garment in part is dictated by the maximum stretch of the compression garment when worn as a property of the materials of the layers of main body, and additionally the circumference of the limb of the user. The limb circumference in turn is a function of the degree of edema and muscle expansion and contraction, which may change with the changing condition of the user, or use conditions such as whether the user is resting or moving. Depending upon the degree by which the user stretches the compression garment around the given limb circumference, different levels of working pressure may be achieved. Typical radial compression or working pressure levels may run from about 20-60 mmHg depending upon the materials being used and the compression needs of the user. The low end of the range also would tend to be the pressure with the user at rest, whereas movement would tend to be associated with working pressures on the higher end of the range. In addition, the limited stretch material may be configured with different portions of the garment being capable of achieving different or graduated levels of compression along the garment.

As referenced above, the main body 12 may be formed of three layers including an internal compressible layer sandwiched between a first woven fabric layer 30 and a second woven fabric layer 32. In exemplary embodiments, the first woven layer has a first color, and the second woven layer has a second color different from the first color (e.g., black and beige, although any colors may be employed). In the figures, the different colors of layers 30 and 32 are denoted by different levels of shading. Additionally or alternatively to different colors, the first and second woven layers may be patterned differently. In general, differences in color and/or pattern between the two woven layers permit two different looks for the compression garment, with the compression garment being reversible such that either woven layer may be the external layer visible when worn as desired by the user.

Generally, the straps are moveable relative to the connecting portion between a first state and a second state so as to reverse the compression garment. Depending upon the precise configuration of the connecting portion, the straps may be moved around the connecting portion to reverse the compression garment. In the example of FIGS. 1 and 2, the connecting portion and the main body may define gaps or slits where the straps extend from the main body, such as for example when the connecting portion has the zig-zag configuration referenced above. With such configuration, the straps are feedable through the connecting portion, such as being inserted through the slits, to reverse the compression garment between the first state and the second state.

Figure 3:
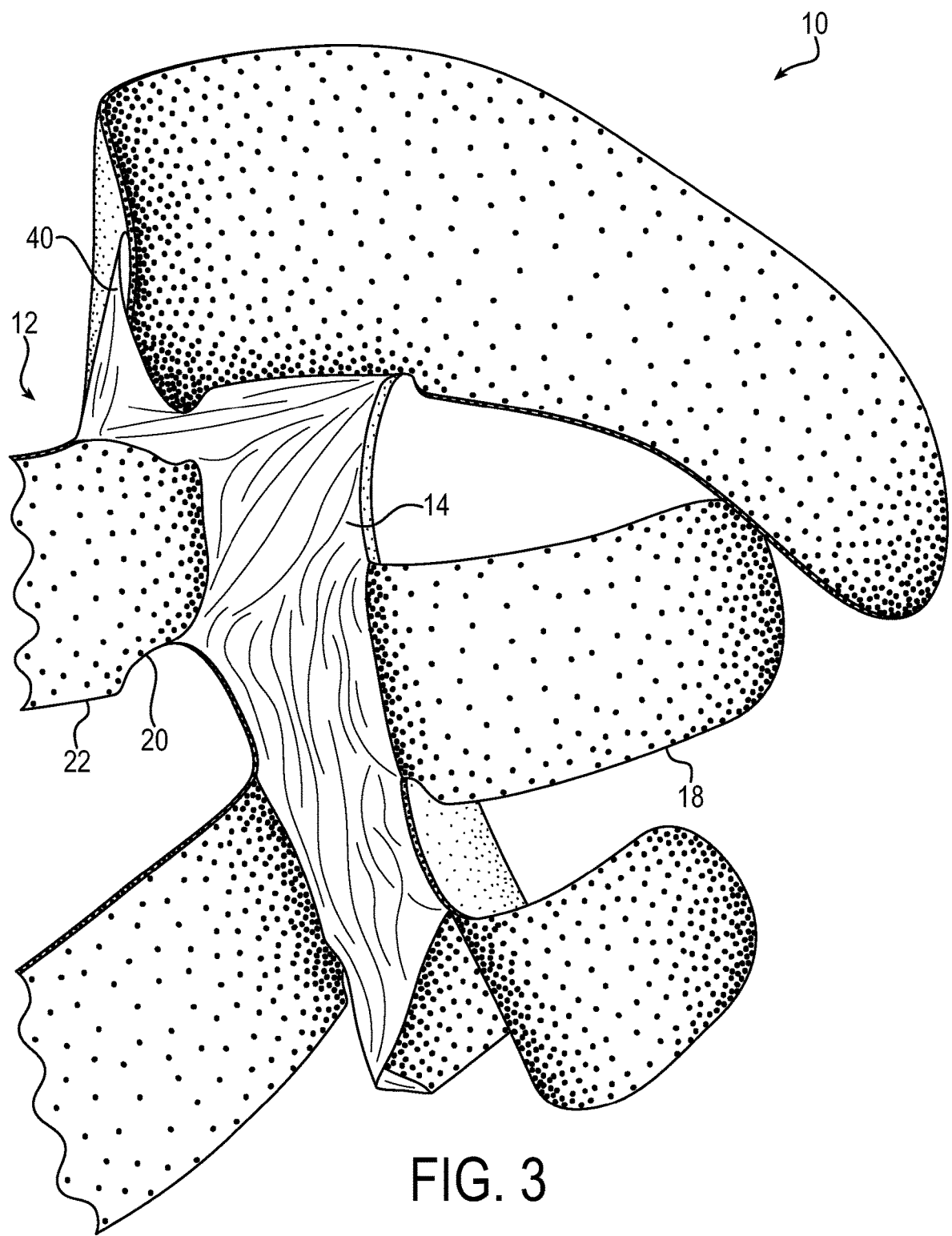
FIG. 3 is another view showing the compression garment, with the compression garment being in an unworn position.
Figure 4:
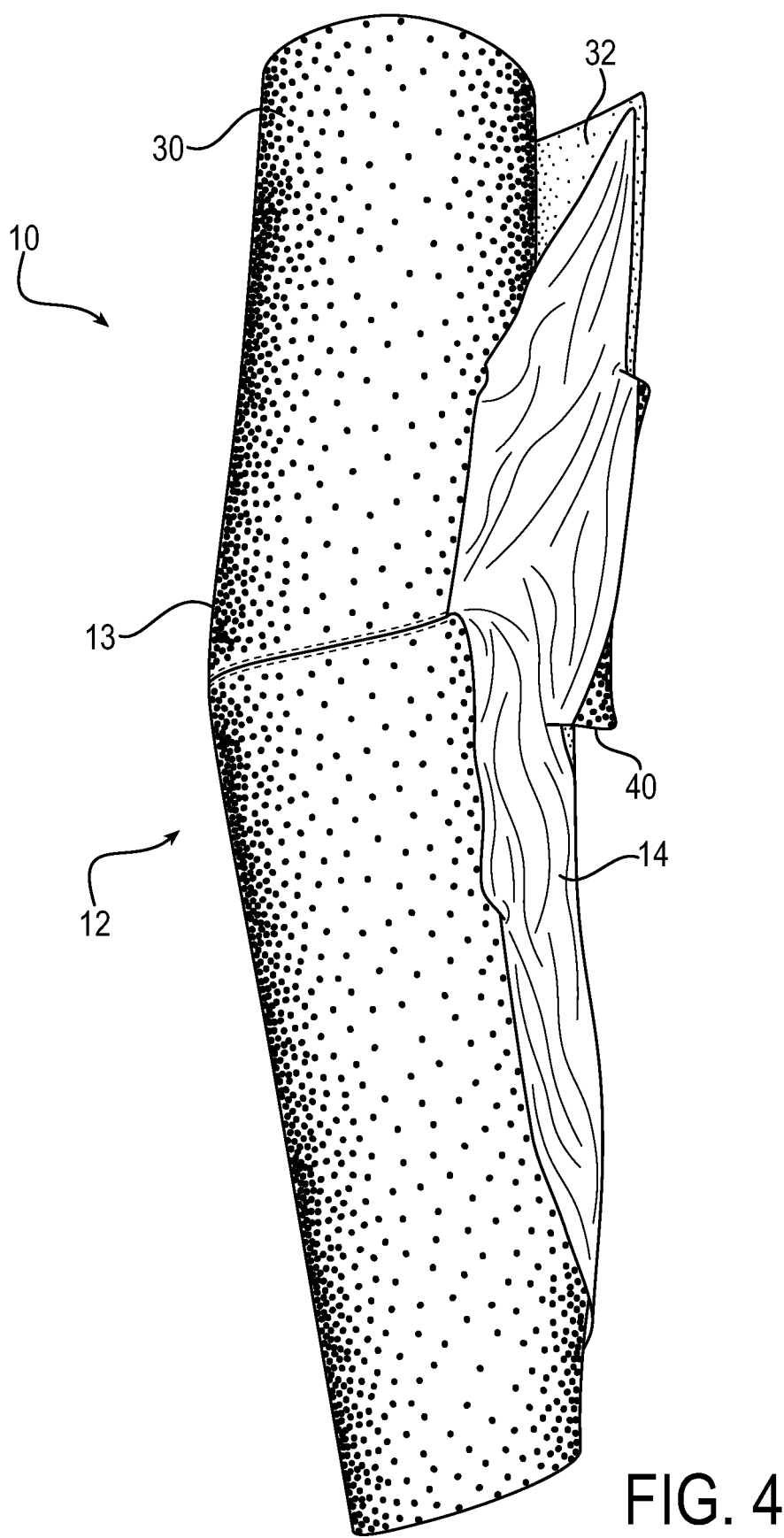
FIG. 4 is a drawing depicting reversing the compression garment to a second state that is reversed relative to the first state.
Figure 5:
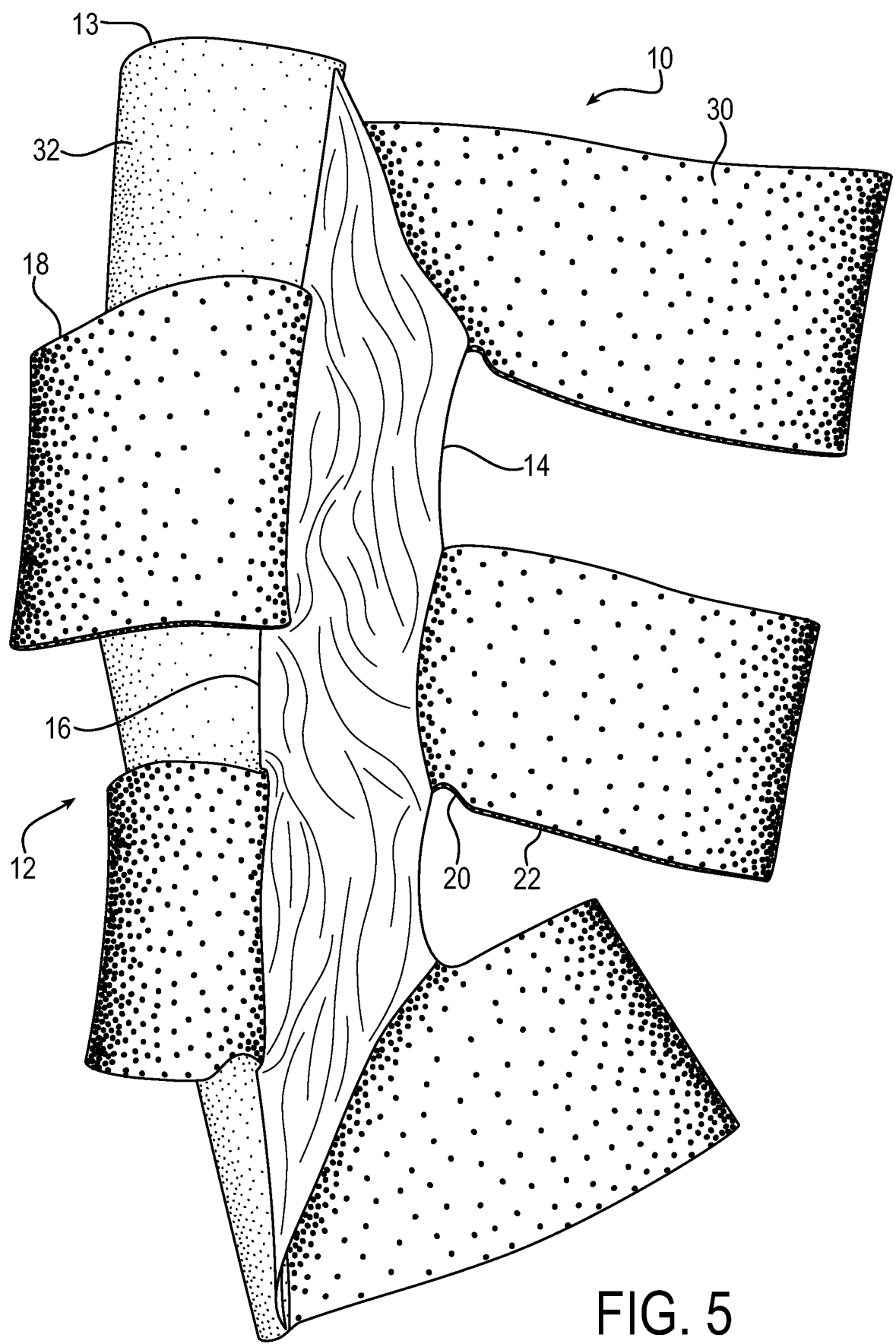
FIG. 5 is a drawing depicting the compression garment in the second state.
Figure 6:
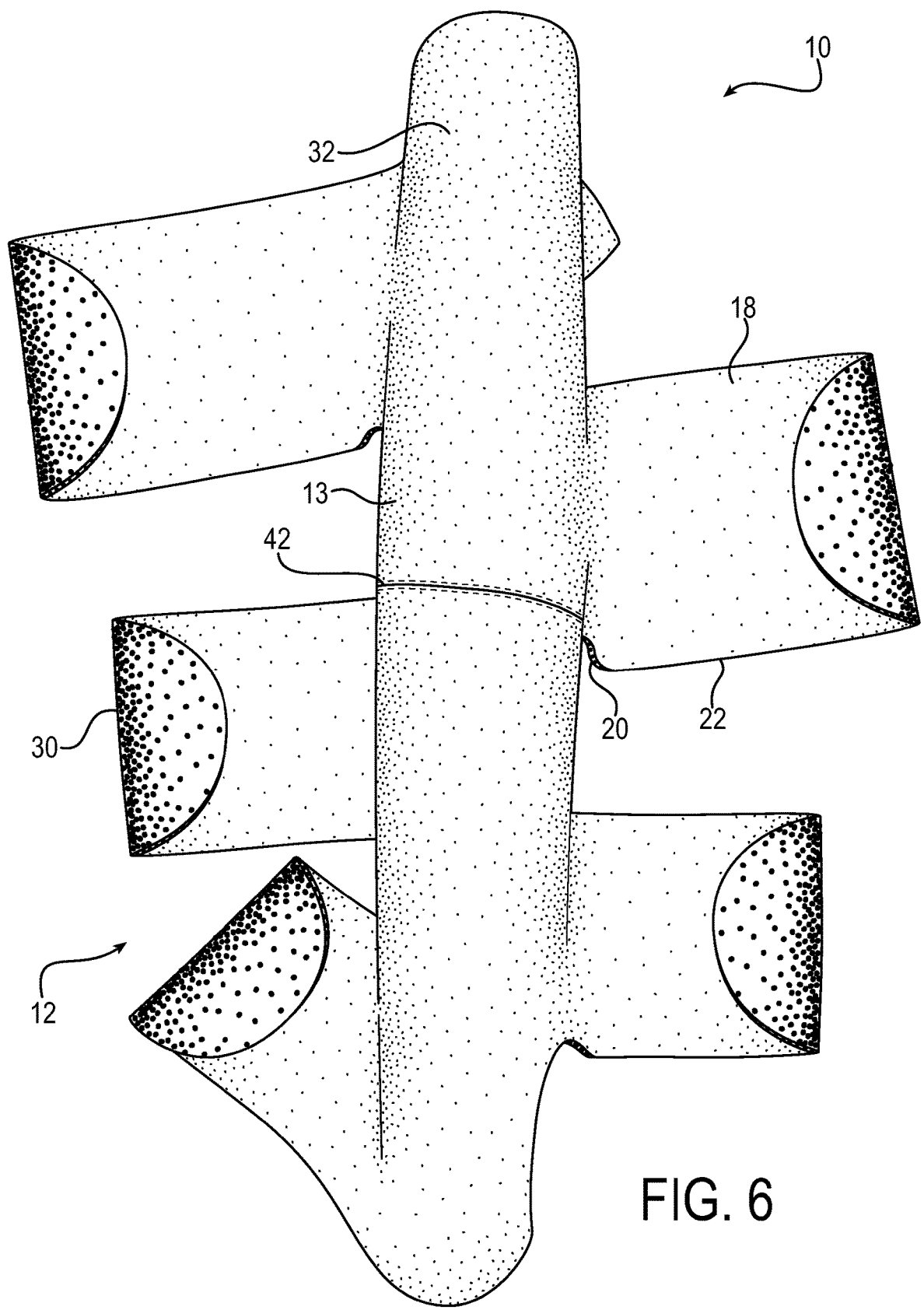
FIG. 6 is a drawing depicting another view of the compression garment in the second state.
Figure 7:
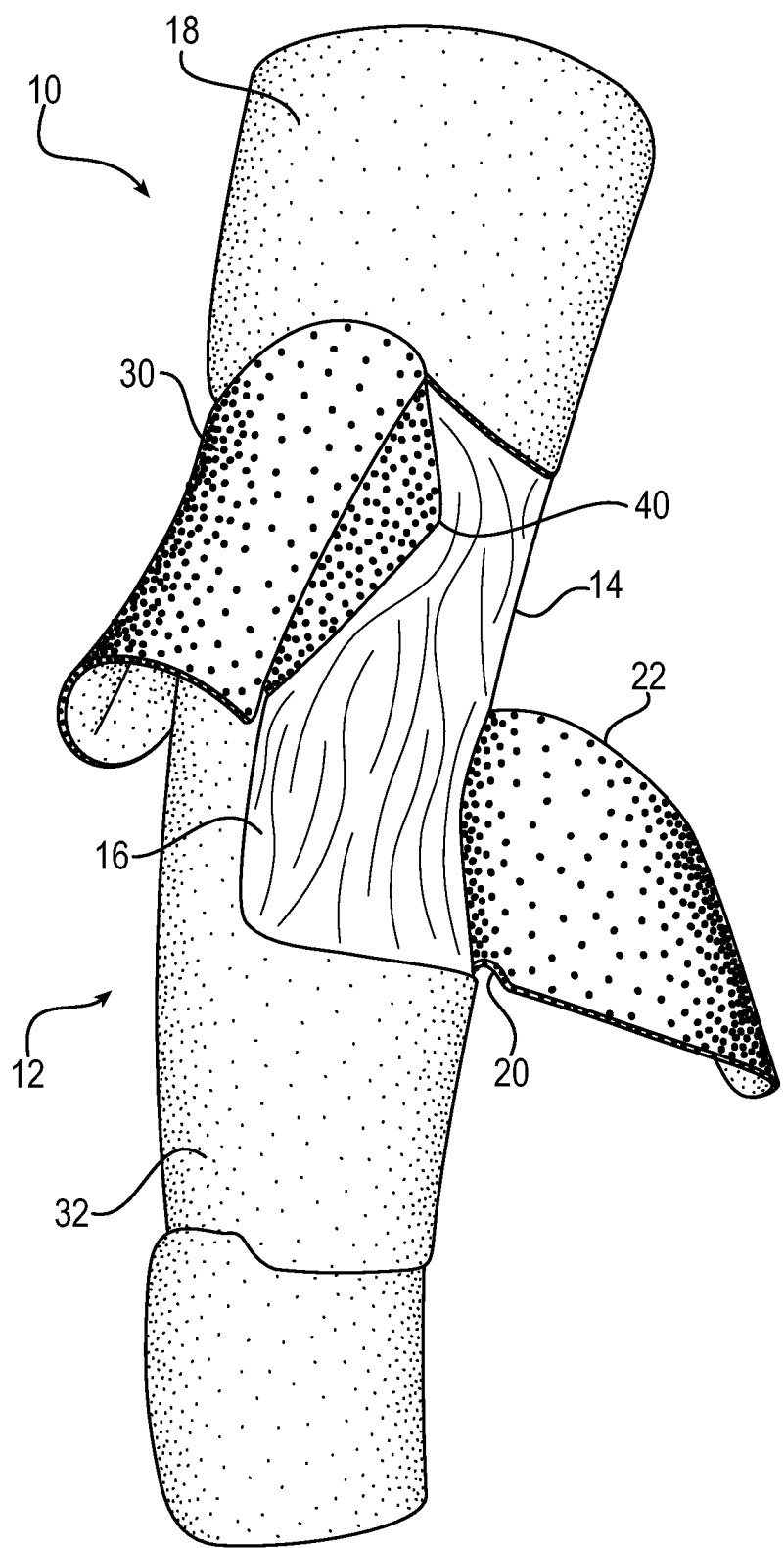
FIG. 7 is a drawing depicting the compression garment with the compression garment being in the second state, as would be worn by a user with the straps partially secured.
Figure 8:
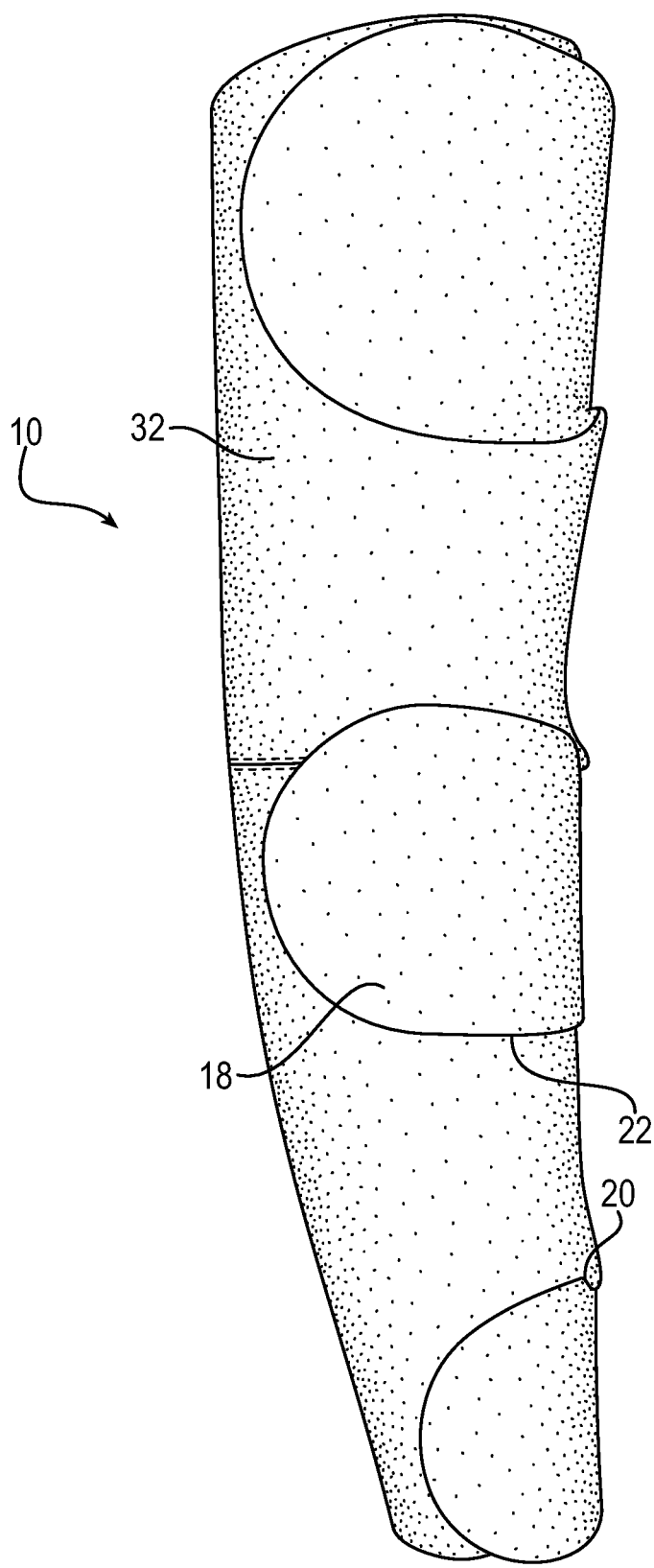
FIG. 8 is a drawing depicting the compression garment with the compression garment being in the second state, as would be worn by a user with the straps fully secured.

In connection with an example of reversibility, therefore, FIG. 1 shows the compression garment in the unworn position laid out in a first state. In such first state, the first woven layer 30 is external relative to the second woven layer 32, i.e., the compression garment will have the look of the first color (or first pattern) when worn in the first state in the depicted example. As seen in FIG. 2, the second woven layer is the inside layer of the straps, which will face inward and not be visible when the straps are secured. FIG. 3 is a drawing depicting another view showing the compression garment in an unworn position. FIGS. 4-6 are drawings depicting reversing the garment from the first state of FIGS. 1-3, with the garment then being in a second state that is reversed relative to the first state. FIGS. 7 and 8 are drawings depicting the compression garment, with the compression garment being in the second state that is reversed relative to the first state as being worn by a user. In such second state, the second woven layer 32 is external relative to the first woven layer 30, i.e., the compression garment will have the look of the second color (or second pattern) when worn in the second state in the depicted example. In the second state, therefore, the first woven layer is then the inside layer of the straps, which will face inward and not be visible when the straps are secured.

In general, as referenced above the straps are moveable relative to the connecting portion between the first state and the second state so as to reverse the compression garment. In the exemplary embodiment of FIGS. 4-8, the straps are feedable through the connecting portion to reverse the compression garment between the first state and the second state. In this exemplary embodiment, the zig-zag nature of the connecting portion 14 creates gaps or slits 40 relative to the main body 12. The slits are seen, for example, in FIGS. 1-3 and 7. In this manner, the connecting portion and the main body define a plurality of slits through which the straps are insertable to reverse the compression garment between the first state and the second state. The gaps or slits in particular are formed in embodiments in which the connecting portion has such a one-piece configuration with a zig-zap shape. Other configurations, however, may be employed that otherwise permit feeding the straps through the connecting portion, moving the straps around the connecting portion, or otherwise moving the straps relative to the connecting portion to reverse the compression garment. For example, when the connecting portion is formed in multiple pieces, the straps may be tucked into the compression garment between the connecting portion pieces and the main body to move the straps through or relative to the connecting portion.

In this particular example, the first step in reversing the garment is to tuck the straps underneath the connecting portion 14, which is shown in FIG. 4. The straps may then be pulled through opposite edges associated with the connecting portion, such as by being inserted through the gaps or slits 40, effectively turning the compression garment inside out relative to the first state of FIGS. 1-3. This inside-out state constitutes the referenced second state, which is shown in FIG. 5. In this second state, the second woven layer 32 (first color or pattern) is now the external layer relative to the first woven layer 30. The first woven layer (first layer or pattern) now is positioned as the inside layer of the straps, which will face inward and will not be visible when the straps are secured by the user. The process may be reversed to configure the garment from the second state of FIG. 5 to the first state of FIGS. 1-3.

FIG. 6 is a drawing depicting the compression garment in the second state of FIG. 5 from a different viewpoint, with a view more of the central portion 13 of the main body. As seen in this example, the central portion may include a seam 42. The seam 42 can provide a biased curvature to the garment for conforming to a wrapped body part for a better fit. In this particular example, the seam 42 is oriented horizontally, which is more suitable to provide a biased curvature for conforming the garment about the elbow. A vertical seam may be more suitable to provide a biased garment curvature for conforming the garment to a lower leg portion about the calf. In addition, in exemplary embodiments the main body can be seamless, which may be suitable for longer limb portions such as wrapping around the thigh.

As described above, FIGS. 5 and 6 illustrate a reversed state of the compression garment relative to FIGS. 1-3, and vice versa. FIG. 7 is a drawing depicting the compression garment as would be donned with the straps partially secured (and again the gaps or slits 40 of the depicted example for manipulating the straps during reversal are shown in this view). FIG. 8 is a drawing depicting the compression garment as would be donned and fully wrapped with the straps secured. The second woven layer 32 (second color or pattern) is now the external layer that is visible. FIGS. 7 and 8 also demonstrate how the notches 20 permit the straps to overlap when the straps are secured in the wrapped position, as described above.

Figure 9:
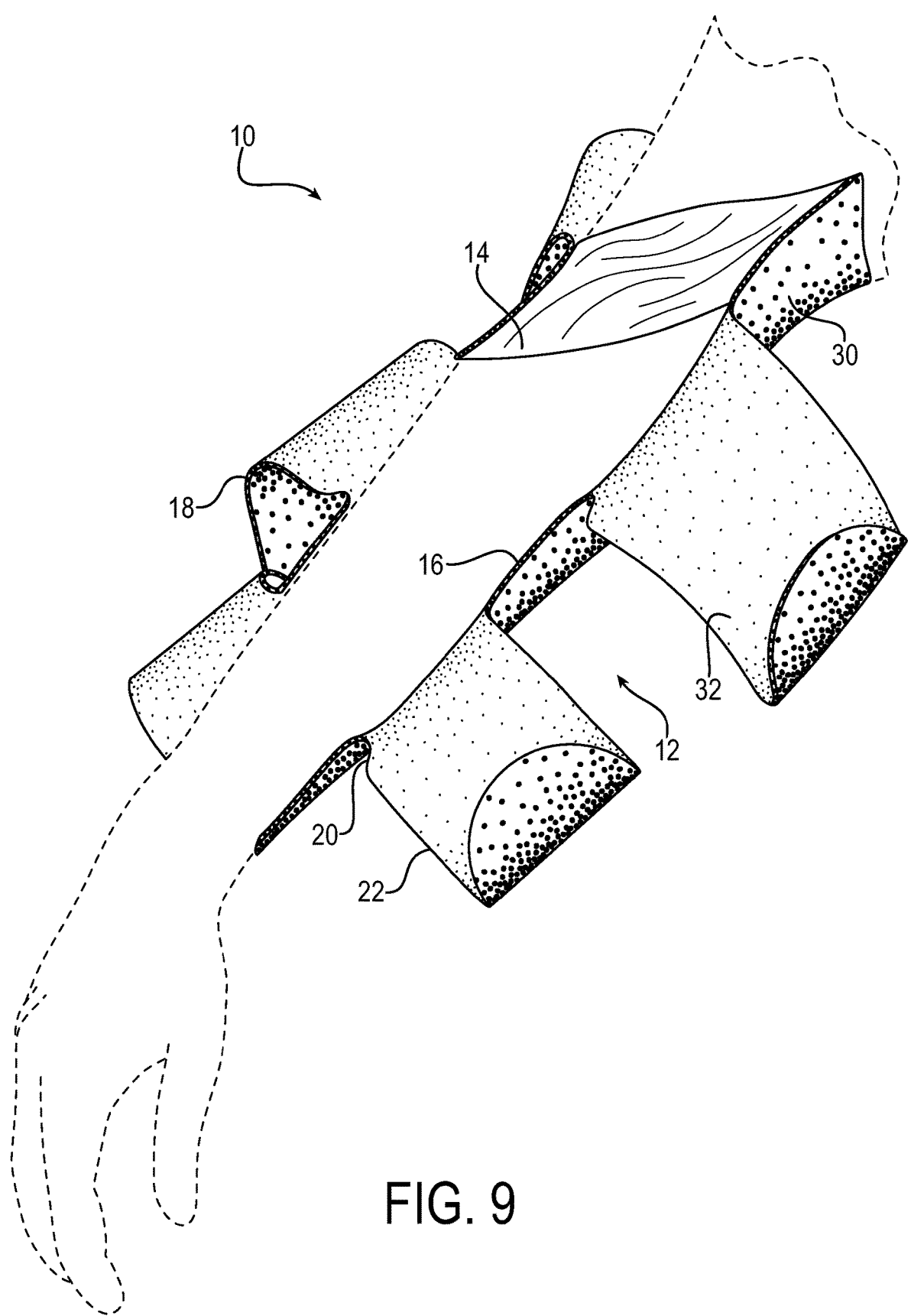
FIG. 9 is a drawing depicting another exemplary configuration of the compression garment in accordance with embodiments of the present invention.

FIG. 9 is a drawing depicting another exemplary configuration of the compression garment 10 in accordance with embodiments of the present invention. The embodiment of FIG. 9 bears similarity to the previous embodiment, except as to the configuration of the connecting portion 14. In the embodiment of FIG. 9, the connecting portion 14 is configured as a single band that extends between opposing second regions of the lateral edge 16 of the main body between straps. In contrast to the zig-zag configuration, the band configuration of FIG. 9 does not form the slits or gaps 40. For reversing the garment, therefore, the straps 18 are moved relative to the connecting portion 14 by moving the straps around the connecting portion.

An aspect the invention is a low-elastic wrapped compression garment that is easy to don and provides suitable compression across a wide range of users and compression needs, and also is reversible to provide two alternative looks of the compression garment. In exemplary embodiments, the compression garment includes a main body including a central portion and a plurality of straps that extend from the central portion; the central portion including a lateral edge, the lateral edge having first regions from which the straps extend from the central portion, and second regions from which the straps do not extend; and a connecting portion that is fixed to the main body, the connecting portion being fixed to at least a portion of the second regions, wherein the straps are moveable relative to the connecting portion to reverse the compression garment between a first state and a second state. The compression garment may include one or more of the following features, either individually or in combination.

In an exemplary embodiment of the compression garment, the straps are moveable around the connecting portion to reverse the compression garment between the first state and the second state.

In an exemplary embodiment of the compression garment, the straps are feedable through the connecting portion to reverse the compression garment between the first state and the second state.

In an exemplary embodiment of the compression garment, the connecting portion and the main body define a plurality of slits through which the straps are insertable to reverse the compression garment between the first state and the second state.

In an exemplary embodiment of the compression garment, the connecting portion comprises a band of material extending between opposing second regions of the main body.

In an exemplary embodiment of the compression garment, the main body and the connecting portion are made of different materials.

In an exemplary embodiment of the compression garment, the connecting portion is thinner and has a higher elasticity relative to the main body.

In an exemplary embodiment of the compression garment, the connecting portion is fixed to the lateral edge across an entirety of the second regions.

In an exemplary embodiment of the compression garment, the connecting portion is fixed to the lateral edge across less than an entirety of the second regions.

In an exemplary embodiment of the compression garment, the connecting portion is a single piece of material fixed to the second regions to form a zig-zag shape.

In an exemplary embodiment of the compression garment, the connecting portion is split into multiple pieces.

In an exemplary embodiment of the compression garment, the main body comprises layers of material including a first woven layer and a second woven layer; and wherein in the first state the first woven layer is external relative to the second woven layer, and in the second state the second woven layer is external relative to the first woven layer.

In an exemplary embodiment of the compression garment, the first woven layer and second woven layer are different colors and/or have different patterns.

In an exemplary embodiment of the compression garment, the compression garment further includes at least one notch where an edge of one of the straps meets the lateral edge of the central portion of the main body; wherein when the compression garment is in a wrapped position, edges of adjacent straps including an edge of the strap that extends from the at least one notch overlap.

In an exemplary embodiment of the compression garment, the at least one notch comprises a plurality of notches, and wherein a notch is provided where an edge of one of the straps meets the lateral edge of the central portion of the main body, wherever an edge of one of the straps that extends from one of the notches overlaps an edge of an adjacent strap that extends from another one of the notches when the compression garment is in the wrapped position.

In an exemplary embodiment of the compression garment, the at least one notch comprises a plurality of notches, and wherein each notch is provided where an edge of one of the straps meets the lateral edge of the central portion of the main body, and each notch receives an opposing straight portion of an edge of an adjacent strap when the compression garment is in the wrapped position.

In an exemplary embodiment of the compression garment, the central portion of the main body includes a seam to provide a biased curvature configured for conforming the compression garment to the limb.

In an exemplary embodiment of the compression garment, the central portion of the main body is seamless.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A compression garment that is to be wrapped around a limb of a user, the compression garment comprising:
    a main body including a first woven layer and a second woven layer, the main body comprising:
    a central portion comprising a first lateral edge and a second lateral edge, the first lateral edge and the second lateral edge being at a periphery of the central portion, wherein the first lateral edge and the second lateral edge comprise a plurality of first regions and a plurality of second regions, and
    a plurality of straps that extend from the first regions of the first lateral edge at the periphery of the central portion and the first regions of the second lateral edge at the periphery of the central portion, wherein the straps extending from the first regions of the first lateral edge are staggered with the straps extending from the first regions of the second lateral edge; and
    a connecting portion that is fixed to the first lateral edge at the periphery of the central portion of at least one of the second regions of the first lateral edge at the periphery of the central portion and fixed to the second lateral edge at the periphery of the central portion of at least one of the second regions of the second lateral edge at the periphery of the central portion,
    wherein the straps are moveable relative to the connecting portion to reverse the compression garment between a first state and a second state, wherein in the first state, the first woven layer of the main body is external relative to the second woven layer when the compression garment is in a wrapped position, and wherein in the second state, the second woven layer of the main body is external relative to the first woven layer when the compression garment is in a wrapped position.

2. The compression garment of claim 1, wherein at least one strap of the plurality of straps is feedable through a slit defined by the connecting portion and the periphery of the main body to reverse the compression garment between the first state and the second state.

3. The compression garment of claim 1, wherein the main body and the connecting portion are made of different materials.

4. The compression garment of claim 3, wherein the connecting portion is thinner and has a higher elasticity relative to the main body.

5. The compression garment of claim 1; wherein the connecting portion is a single piece of material fixed to the second regions of the first lateral edge and the second regions of the second lateral edge to form a zigzag shape.

6. The compression garment of claim 1, wherein the first woven layer and second woven layer are different colors and/or have different patterns.

7. The compression garment of claim 1, further comprising at least one notch where an edge of one of the straps meets the first lateral edge and/or the second lateral edge;
    wherein when the compression garment is in a wrapped position, edges of adjacent straps, including an edge of the strap that extends from the at least one notch, overlap.

8. The compression garment of claim 7, wherein the at least one notch comprises a plurality of notches, and wherein:
    a notch is provided where an edge of one of the straps meets the first lateral edge and/or the second lateral edge, an edge of one of the straps that extends from one of the notches overlaps an edge of an adjacent strap that extends from another one of the notches when the compression garment is in the wrapped position.

9. The compression garment of claim 7, wherein the at least one notch comprises a plurality of notches, and wherein:
each notch is provided where an edge of one of the straps meets the first lateral edge and/or the second lateral edge, and each notch receives an opposing straight portion of an edge of an adjacent strap when the compression garment is in the wrapped position.

10. The compression garment of claim 1, wherein the central portion of the main body includes a seam to provide a biased curvature configured for conforming the compression garment to the limb.

11. A compression garment that is to be wrapped around a limb of a user, the compression garment comprising:
a main body including a first woven layer and a second woven layer, the main body comprising:
a central portion comprising a first lateral edge and a second lateral edge, wherein the first lateral edge and the second lateral edge comprise a plurality of first regions and a plurality of second regions, and
a plurality of straps that extend from the first regions of the first lateral edge and the first regions of the second lateral edge, wherein the straps extending from the first regions of the first lateral edge are staggered with the straps extending from the first regions of the second lateral edge; and a connecting portion that is fixed to at least one of the second regions of the first lateral edge and at least one of the second regions of the second lateral edge,
wherein the straps are moveable relative to the connecting portion to reverse the compression garment between a first state and a second state,
wherein in the first state, the first woven layer of the main body is external relative to the second woven layer and the straps overlie the connecting portion when the compression garment is in a wrapped position such that when the first state is worn by the user the connecting portion is configured to be between the limb of the user and the straps, and
wherein in the second state, the second woven layer of the main body is external relative to the first woven layer and the straps overlie the connecting portion when the compression garment is in a wrapped position such that when the second state is worn by the user the connecting portion is configured to be between the limb of the user and the straps.

12. The compression garment of claim 11, wherein at least one strap of the plurality of straps is feedable through a slit defined by the connecting portion and the main body to reverse the compression garment between the first state and the second state.

13. The compression garment of claim 11, wherein the main body and the connecting portion are made of different materials.

14. The compression garment of claim 13, wherein the connecting portion is thinner and has a higher elasticity relative to the main body.

15. The compression garment of claim 11, wherein the first woven layer and second woven layer are different colors and/or have different patterns.

16. The compression garment of claim 11, wherein the central portion of the main body includes a seam to provide a biased curvature configured for conforming the compression garment to the limb.

17. A compression garment that is to be wrapped around a limb of a user, the compression garment comprising:
a main body including a first woven layer and a second woven layer, the main body comprising:
a central portion comprising a first lateral edge and a second lateral edge, wherein the first lateral edge and the second lateral edge comprise a plurality of first regions and a plurality of second regions, and a plurality of straps that extend from the first regions of the first lateral edge and the first regions of the second lateral edge, wherein the straps extending from the first regions of the first lateral edge are staggered with the straps extending from the first regions of the second lateral edge; and
a connecting portion that is fixed to at least one of the second regions of the first lateral edge and at least one of the second regions of the second lateral edge, wherein a lateral edge of the connecting portion at a periphery of the connecting portion and at least one of the first lateral edges of the central portion from which at least one strap of the plurality of straps extends form a slit through which the at least one strap of the plurality of straps is feedable to reverse the compression garment between a first state and a second state,
wherein in the first state, the first woven layer of the main body is external relative to the second woven layer and the straps overlie the connecting portion when the compression garment is in a wrapped position such that when the first state is worn by the user the connecting portion is configured to be between the limb of the user and the straps, and
wherein in the second state, the second woven layer of the main body is external relative to the first woven layer and the straps overlie the connecting portion when the compression garment is in a wrapped position such that when the second state is worn by the user the connecting portion is configured to be between the limb of the user and the straps.

18. The compression garment of claim 17, wherein the straps overlie the connecting portion when the compression garment is in a wrapped position.

19. The compression garment of claim 17, wherein the main body and the connecting portion are made of different materials.

20. The compression garment of claim 17, wherein the first woven layer and second woven layer are different colors and/or have different patterns.

* * * * *